(12) United States Patent
Tallon

(10) Patent No.: US 6,838,198 B2
(45) Date of Patent: Jan. 4, 2005

(54) ORGANIC/INORGANIC-OXIDE MULTILAYER MATERIALS

(75) Inventor: Jeffery Tallon, Wellington (NZ)

(73) Assignee: Industrial Research Limited, Auckland (NZ)

(*) Notice: Subject to any disclaimer, the term of this patent is extended or adjusted under 35 U.S.C. 154(b) by 114 days.

(21) Appl. No.: 10/010,746

(22) Filed: Dec. 7, 2001

(65) Prior Publication Data

US 2002/0121700 A1 Sep. 5, 2002

(30) Foreign Application Priority Data

Dec. 7, 2000 (NZ) .................................................. 508699

(51) Int. Cl.[7] ................................................. B32B 9/00
(52) U.S. Cl. ......................... 428/702; 408/98; 408/189; 408/330; 408/900
(58) Field of Search ........................... 428/44, 98, 189, 428/330, 702, 900, 402; 156/73.1, 290, 308.4, 553, 580.1, 580.2

(56) References Cited

U.S. PATENT DOCUMENTS

| | | | | |
|---|---|---|---|---|
| 4,376,709 A | * | 3/1983 | Johnson et al. ................. 252/1 |
| 4,964,016 A | * | 10/1990 | Marchand et al. ....... 361/321.4 |
| 4,980,333 A | * | 12/1990 | Landis et al. ................ 502/246 |
| 5,463,042 A | * | 10/1995 | Pinnavaia et al. ........... 540/139 |
| 5,882,548 A | * | 3/1999 | Liang et al. ............ 252/301.16 |
| 6,180,956 B1 | * | 1/2001 | Chondroudis et al. ......... 257/40 |
| 6,384,253 B1 | * | 5/2002 | Khan ........................... 556/44 |
| 6,420,056 B1 | * | 7/2002 | Chondroudis et al. ...... 428/690 |
| 6,429,318 B1 | * | 8/2002 | Mitzi ............................. 549/3 |
| 6,592,991 B1 | * | 7/2003 | Wiesner et al. ............. 428/404 |

OTHER PUBLICATIONS

P. Yam, "Plastics Get Wired", *Scientific American*, pp. 75–79 (Jul. 1995).

J.C. Scott, "Conducting Polymers: From Novel Science to New Technology", *Science*, vol. 278, pp. 2071–2072 (Dec. 19, 1997).

R.F. Service, "Getting a Charge Out of Plastics", *Science*, vol. 290, pp. 425–427, (Oct. 20, 2000).

J.S. Miller, "Conducting Polymers—Materials of Commerce", *Advanced Materials*, vol. 5, pp. 587–589 & 671–676, (1993).

\* cited by examiner

*Primary Examiner*—H. Thi Le
(74) *Attorney, Agent, or Firm*—Dann, Dorfman, Herrell and Skillman, P.C.

(57) ABSTRACT

The present invention relates to novel organic/inorganic-oxide multilayer materials. In particular novel organic/inorganic-oxide materials based on single or multiple atomic layers of tungsten oxide, molybdenum oxide or other metal oxides interspersed between organic spacer layers is disclosed along with a method of preparing the materials, preferably via self assembly.

69 Claims, 10 Drawing Sheets

US 6,838,198 B2

ORGANIC/INORGANIC-OXIDE MULTILAYER MATERIALS

FIELD OF INVENTION

The present invention relates to novel organic/inorganic-oxide multilayer materials. More particularly but not exclusively the invention relates to novel organic/inorganic-oxide materials based on single or multiple atomic layers of tungsten oxide, molybdenum oxide or other metal oxides interspersed between organic spacer layers.

BACKGROUND

The development of organic conductors and semiconductors in recent decades has opened the door to the possibility of flexible plastic displays and low-cost logic and storage devices [see for example P. Yam, 'Plastics get wired.' *Scientific American*, 273 (1), 74–79 (July 1995), or J. C. Scott, 'Conducting polymers: From novel science to new technology,' *Science*, 278 (5346). 2071–2072 (Dec. 12, 1997).]. There is much international effort to push these materials through to practical devices [see for example the above noted references or: J. S. Miller, 'Conducting Polymers—materials of commerce', *Advanced Materials*, 5 (7/8 & 9), 587–589 & 671–676, (1993).]. The overwhelming significance of these developments has been recognised by the award of the Nobel Prize in Chemistry for the year 2000 to MacDiarmid, Heeger and Shirakawa, the discoverers of the conducting a polymer polyacetylene [see for example R. F. Service 'Getting a Charge Out of Plastics' *Science*, 290, 425–427, (Oct. 20, 2000)]. However, a significant limitation in the use of organic semiconductors is their low electron mobility arising from the weak van der Waals bonding between neighbouring polymer molecules. This, in turn, limits device switching speeds. High electron mobility can be found in doped crystalline inorganic oxides (because of their strong covalent bonding of their extended framework) but these materials demand high temperatures for synthesis and are brittle, non-flexible materials.

A specific example of such an oxide material is tungsten trioxide, $WO_3$. This material adopts a wide range of electronic properties ranging from an n-type semiconductor to a metal depending upon doping level. These doping states are accompanied by the well-known changes in colour observed in the so-called tungsten bronzes that have been used, for example, in pigments for paint. More advanced applications include architectural glazings, ophthalmic devices, instrumentation devices and displays. Tungsten trioxide has a perovskite $ABO_3$ structure with the usually 12-coordinated A-sites vacant, consistent with the 6+ valence state of $W^{6+}$. Each W ion is 6-fold coordinated to oxygen atoms in a roughly octahedral coordination. The octahedra are corner shared as shown by the schematic section in FIG. 1 where the octahedra are represented by the corner shared diamonds. Electron doping into the conduction band is achieved by inserting additional cations into the otherwise vacant 12-coordinated A sites. Molybdenum trioxide, $MoO_3$, exhibits much the same chemistry and structure. (While $ABO_3$ is the usual generalisation of the perovskite formula the identifier "A" will be used in the following to describe general organic groups. To avoid confusion the general formula $ZMO_3$ will be used in place of $ABO_3$ where Z refers to the 12-coordinated perovskite site and M refers to the 6-coordinated approximately octahedral site).

OBJECT OF THE INVENTION

It is an object of the present invention to provide novel materials and methods for preparing such materials, exhibiting electron mobility/conductivity characteristics. It is an additional/alternative object to provide a novel material for application as a semiconductor and/or superconductor. It is an additional/alternative object to provide the public with a useful alternative.

SUMMARY OF INVENTION

In a first aspect of the invention there is provided a layered organic-inorganic oxide material comprising or including:

one or more layers of metal oxide consisting of one or more atomic planes of corner-shared $MO_6$ octahedra, where M is the metal, and one or more layers of organic molecules, wherein the metal-oxide layers alternate with one or more organic layers alternate to form a periodic planar structure.

Preferably, the metal M is W, V or Mo, or a combination of these.

Preferably the metal M is metal M is W, V or Mo, or a combination of these and wherein other high valency metals such as Ti, Nb, Ta, Ru and Re are used in partial combination with Mo, W or V.

Preferably the material a general formula $X.M_mO_{3m+1}$ wherein M is the metal, and X is an organic cation and m=1, 2, 3.

Preferably the organic cation is bidentate.

Preferably the configuration of organic layer relative to the inorganic layer is eclipsed.

In one form the organic cation is a diammonium cation, the material is of composition $NH_3.A.NH_3.M_mO_{3m+1}$.

Preferably m=1, such that each inorganic oxide atomic plane alternates with an organic layer; alternatively m=2, the composition is $NH_3.A.NH_3.M_2O_7$ and wherein the organic oxide exists as a double atomic plane layer of corner shared $MO_6$ octahedra, such that the material has the stacking structure —A—O—$MO_2$—O—$MO_2$—O—A.

Preferably the organic cation is an aliphatic diammonium cation, and $A=(CH)_n$, n=1, 2 . . . .

Preferably on the organic cation the ammonium cation groups are positioned on the terminal alkane units of A.

In another form the material has the chemical formula $NH_3(CH_2)_nNH_3MO_4$.

Preferably with n=2 or 6 or 12.

Preferably the organic cation is an aromatic diammonium cation.

Preferably $A=C_6H_4$ and the organic cation is $NH_3C_6H_4NH_3$.

Alternatively the organic cation comprises an aromatic ring with two aliphatic side chains of equal or unequal length each side chain terminated by an ammonium ion, the organic cation having the general formula $NH_3(CH_2)_nC_6H_4(CH_2)_mNH_3$.

Preferably adjacent aromatic rings are crosslinked to form an organic polymer layer.

Preferably the organic polymer layer is conducting.

In another form the material has a general formula $X'_2.M_mO_{3m+1}$ wherein M is the metal, and X' is an organic cation and m=1, 2, 3.

Preferably the organic cation is monodentate.

Preferably the configuration of organic layer relative to the inorganic layer is staggered.

Preferably both organic cations are monoammonium cations and the material is of composition $(NH_3.A')_2.M_mO_{3m+1}$.

Preferably m=1, such that each inorganic oxide atomic layer alternates with an organic layer.

Alternatively m=2, the composition is $(NH_3.A')_2.M_2O_7$ and wherein the organic oxide exists as a double atomic plane layer having approximately the $ZWO_3$ perovskite structure with the Z sites vacant such that the material has the stacking structure $NH_3.A'—MO_2—O—MO_2—A'.NH_3$.

Preferably one or both organic cation is an aliphatic ammonium cation, and $A'=(CH)_n$, $n=1, 2, \ldots$ Alternatively one or both organic cation is an aromatic ammonium cation.

Preferably the aromatic ring has a side chain which is aliphatic and terminated by an ammonium ion, having the formula $(C_6H_5.(CH_2)_m NH_3)_2 MO_4$ where $m=0, 1, 2, 3, \ldots$ Preferably adjacent aromatic rings are crosslinked to form an organic polymer layer.

Preferably the organic polymer layer is conducting.

Preferably dopants are introduced into the structure.

Preferably the dopant is selected from one or more of an alkali cation a methylammonium cation, replacing ammonium groups, field-effect injected electrons or field-effect injection electron holes.

Preferably the dopant is present in the inorganic oxide layers and the doping state of the oxide is adjusted such that the oxide exhibits superconductivity above the temperature of 40K.

Preferably the doping state of the oxide is adjusted such that the oxide exhibits superconductivity above the temperature of 90K.

Preferably M is partially or fully substituted by a magnetic transition metal ion so as to display magnetically ordered states.

In a further embodiment there is provided an organic/inorganic oxide material of any of claims 1 to 33 in which the oxide layer comprising $MO_4$, $M_2O_7$ or $M_mO_{3m+1}$ is wholly replaced by any of the following oxide layers $CuO_2$, $NiO_2$, $CoO_2$, $CuCO_2CaCuO_2$, $Ca_{m-1}Cu_mO_{2m}$, $m=1, 2, 3, \ldots$, $NiO_2CaNiO_2$, $Ca_{m-1}Ni_mO_{2m}$, $m=1, 2, 3, \ldots$, square pyramidal $MnO_3$, square pyramidal $RuO_3$, octahedral $RuO_4$, $O—MnO_2—Y—MnO_2—O$, $O—MnO_2—Ca—MnO_2—O$, $O—RuO_2—Y—RuO_2—O$, or $O—RuO_2—Ca—RuO_2—O$.

According to a further aspect of the invention there is provided a layered organic-inorganic oxide material comprising or including:

One or more layers of metal oxide consisting of one or more atomic planes of metal oxide having substantially the $ZMO_3$ perovskite structure (M=metal) with the Z sites vacant, and one or more layers of organic molecules, wherein the metals form divalent cations and are coordinated into a corner-shared square-planar structure, or wherein the metals form tetravalent cations and are coordinated into a corner-shared square-pyramid structure, wherein one or more metal-oxide layers alternate with one or more organic layers alternate to form a periodic planar structure.

Preferably the metal, M, is Cu, Ni, Ru, Mn, or a combination of these.

Preferably higher order structures are formed with two or more oxide layers each separated by an al earth ion which is situated in the perovskite A-site.

Preferably the alkali earth ion is calcium.

Preferably the material has the general formula of one of: $NH_3.A.NH_3CuO_2$, $(A.NH_3)_2CuO_2$, $NH_3.A.NH_3Ca_{m-1}Cu_mO_{2m}$, $m=1, 2, 3, \ldots$, $(ANH_3)_2Ca_{m-1}Cu_mO_{2m}$, $m=1, 2, 3, \ldots$, $NH_3.A.NH_3NiO_2$, $(A.NH_3)_2NiO_2$, $NH_3.A.NH_3Ca_{m-1}Ni_mO_{2m}$, $m=1, 2, 3, \ldots$, $(A.NH_3)_2Ca_{m-1}Ni_mO_{2m}$, $m=1, 2, 3, \ldots$, and $NH_3.A.NH_3MnO_3$, $(A.NH_3)_2MnO_3$, $NH_3.A.NH_3Ca_{m-1}Mn_mO_{2m+2}$, $m=1, 2, 3, \ldots$, $(A.NH_3)_2Ca_{m-1}Mn_mO_{2m+2}$, $m=1, 2, 3, \ldots$, $NH_3.A.NH_3RuO_3$, $(A.NH_3)_2RuO_3$, $NH_3.A.NH_3Ca_{m-1}Ru_mO_{2m+2}$, $m=1, 2, 3, \ldots$, $(A.NH_3)_2Ca_{m-1}Ru_mO_{2m+2}$, $m=1, 2, 3, \ldots$.

Preferably dopants are introduced into the structure.

Preferably the dopant is selected from one or more of an alkali cation a methylammonium cation, replacing ammonium groups, field-effect injected electrons or field-effect injection electron holes.

Preferably the dopant is present in the inorganic oxide layers and the doping state of the oxide is adjusted such that the oxide exhibits superconductivity above the temperature of 40K.

Preferably the doping state of the oxide is adjusted such that the oxide exhibits superconductivity above the temperature of 90K.

Preferably M is partially or fully substituted by a magnetic transition metal ion so as to display magnetically ordered states.

According to a tinter aspect of the invention there is provided a method of preparing a layered inorganic-organic material which comprises or includes:

one or more layers of metal oxide, and one or more organic layers, wherein the layers exist substantially in a perovskite structure, the method comprising or including the steps of contacting a source of metal and/or oxide with a source of the organic layer such that the layer structure substantially self assembles.

Preferably the material is of the general structure $NH_3.A.NH_3.M_mO_{3m+1}$ and is prepared either:

by reaction of a diaminoalkane with tungstic acid (when the metal is W) or molybdic acid (when the metal is Mo), or by dissolution of tungstic acid (when the metal is W) or molybdic acid (when the metal is Mo) ammonia solution, or by reaction of W or Mo metal with hydrogen peroxide.

According to a further aspect of the invention there is provided a layered inorganic-organic material prepared substantially according to the above method.

According to a further aspect of the invention there is provided a method of preparing a layered inorganic-organic material comprising or including One or more layers of metal oxide consisting of one or more atomic planes of metal oxide having substantially the $ZMO_3$ perovskite structure, or derivatives/analogues thereof (M=metal) with the Z sites vacant, and one or more layers of organic molecules, wherein one or more metal-oxide layers alternate with one or more organic layers alternate to form a periodic planar structure, and wherein the spacing and electronic coupling between adjacent but separation inorganic layers can be preselected by choice of appropriate organic molecule.

According to a further aspect of the invention there is provided a layered inorganic-organic material prepared substantially according to the above methods.

DETAILED DESCRIPTION OF THE INVENTION

The present invention describes novel self-assembling organic/inorganic-oxide multilayer materials based on single or multiple atomic layers of tungsten oxide, molybdenum oxide or other metal oxides interspersed between organic spacer layers. These provide "plastic-like" materials with highly tuneable electronic properties suitable for electronic applications and especially flexible displays, electrochromic devices, sensors and logic and storage devices. In addition the two-dimensional character of these hybrid multilayers offers the possibility of a broad range of other applications including thermoelectric coolers and possibly novel superconductors. The invention also encompasses other similar organic/inorganic multilayer materials based on copper, nickel, manganese or ruthenium oxides which display exotic quasi-two-dimensional magnetic properties and superconductivity. The simplicity of their self-assembly, using solution-based fabrication, provides for a cost-advantage technology with all the benefits of plastics, especially flexibility and ease of manufacture.

The present invention, by way of example, is directed to the fabrication of materials comprising two-dimensional single atomic layers of corner-shared $WO_6$ octahedra interspersed between organic spacer layers. Such a material offers the high electron mobility associated with the extended $WO_6$ sheets together with the flexibility associated with the organic spacer layers which facilitate the self-assembly of the hybrid materials. Such atomically layered materials further provide enhanced and exotic electronic properties associated with the low dimensionality of the $WO_6$ sheets.

When a single atomic layer of $WO_6$ octahedra is formed then its chemical formula is $WO_4^{2-}$ (the four in-plane oxygens all being shared by adjacent octahedra while the two apical oxygens are confined wholly to a single octahedron). Thus two additional cation charges need to be supplied per formula unit to stabilise the structure. In the present invention these additional charges (providing the charge balance) are introduced using ammonium ions positioned in the vacant A-sites above and below the $WO_4^{2-}$ layer. These ammonium ions may terminate each end of an organic molecule as illustrated schematically in FIG. 2 with the structure repeated indefinitely in the c-direction providing an organic/inorganic multilayered hybrid material where the organic spacer layer is a diammonium organic cation. Such a structure possesses highly anisotropic properties and strong two-dimensional in-plane electronic properties. The organic spacer molecules may be, for instance, a diammoniumalkane cation generally represented as $NH_3(CH_2)_n NH_3^{2+}$ and the hybrid compound may be synthesized for example by reacting a diaminoalkane with tungstic acid in solution, viz:

$NH_2(CH_2)_n NH_2 + H_2WO_4 \rightarrow (CH_2)_n(NH_3)_2WO_4$

We may read Mo (molybdenum) or Vanadium for W (tungsten) in all of the above considerations or these may be used in combination. Furthermore other high valency metals such as Ti, Nb, Ta, Ru and Re may be used in partial combination with Mo, W or V. Other known diammonium organic ions will also provide possible stabilising organic spacer molecules. For synthesis in solution tungstic (or molybdic) acid may be dissolved in ammonia solution or, alternatively, the metals W or Mo may be reacted with hydrogen peroxide to form peroxo polytungstate or peroxo polymolybdate acids as precursors. Other standard solution precursors for the metal oxide species will be known in the art.

Further novel compounds of the invention include higher-order organic/inorganic-oxide materials. These comprise multilayers of two or more adjacent sheets of $WO_6$ or $MoO_6$ octahedra separated by the organic spacer layer. Such materials are of general formula $NH_3ANH_3 \cdot W_m O_{3m+1}$ where m=1, 2, 3, or, more specifically in the case of a diammoniumalkane spacer molecule, $NH_3(CH_2)_n NH_3 \cdot W_m O_{3m+1}$ where m=1, 2, 3. A two-layer compound of this sort is shown schematically in FIG. 3.

The novel material structures shown in FIGS. 2 and 3 may be described as eclipsed structures where the octahedra are aligned along the c-axis each in one layer positioned directly above those in adjacent layers across the organic layer. The organic molecules in such materials as described above have two active radical sites (two ammonium groups) and are referred to as bidentate. The invention also comprises a class of staggered organic/inorganic-oxide hybrid materials where the octahedra in adjacent layers are staggered in alignment. Here the organic spacer molecules may be are monoammonium organic molecules, $A.NH_3^+$, which contain a single ammonium group and may be referred to as monodentate. These may stack in interdigitated configuration, with weak bonding between the organic molecules, to provide staggered oxide layers as shown in FIG. 4

The monodentate organic ammonium ions in these structures may comprise an alkyl ammonium ion, $CH_3(CH_2)_m NH_3^+$ with m=1, 2, 3, ... 12, or an aromatic ammonium ion such as benzyl ammonium ion $C_6H_5CH_2NH_3^+$ or phenethyl ammonium ion $C_6H_5CH_2CH_2NH_3^+$. Again higher-order structures, of general formula $(A.NH_3)_2 W_n O_{3n+1}$, are included in the invention in which two or more oxide layers may be interspersed between the organic spacer layers. A schematic example of the n=2, double layer compound is shown in FIG. 5. The organic/inorganic-oxide hybrid compounds may be synthesized from solution using tungstic acid (or molydbic acid) and benzyl amine or phenethylamine.

It can be seen that these novel organic/inorganic-oxide compounds provide great structural diversity which allows considerable control of the coupling between the oxide layers and hence the degree of anisotropy and the effective dimensionality of the electronic states. Moreover, as noted they may be constructed using W, Mo, V or any combination thereof and in addition other metallic cations such as Ti, Nb, Ta, Re and Ru, or other suitable metal, may be incorporated to stabilise the structures and enhance their chemical stability, as well as dope the oxide layers to provide semi-conducting or metallic properties. Electronic doping may also be achieved through incorporation of organic dopants such as methyl ammonium ions. They may be doped by intercalating alkali ions, by electrochemical redox of the organic spacer molecules or by field-effect insertion of carriers in a three-terminal device such as a field-effect transistor, as is known in the art.

Further novel cuprate, nickelate, ruthenate and manganese-based organic/inorganic hybrids are also included in the invention. The basic structure of the materials described above is contingent upon the octahedral oxygen coordination of a hexavalent cation such as $W^{6+}$ or $Mo^{6+}$. Organic/inorganic-oxide structures may be fabricated with divalent cations such as $Cu^{2+}$ and $Ni^{2+}$ where these are coordinated into a corner-shared square-planar structure (i.e. with no apical oxygen) or with tetravalent cations such as $Mn^{4+}$ or $Ru^{4+}$ where these are coordinated into a corner-shared square-pyramid structure. In both cases higher order structures with two or more oxide layers each separated by an alkali earth ion, preferably calcium, situated in the perovskite A-site, may be fabricated. The general formulae for these additional novel materials are $NH_3.A.NH_3CuO_2$, $(A.NH_3)_2CuO_2$, $NH_3.A.NH_3Ca_{m-1}Cu_mO_{2m}$, m=1, 2, 3, ..., $(A.NH_3)_2Ca_{m-1}Cu_mO_{2m}$, m=1, 2, 3, ..., $NH_3.A.NH_3NiO_2$, $(A.NH_3)_2NiO_2$, $NH_3.A.NH_3Ca_{m-1}Ni_mO_{2m}$, m=1, 2, 3, ..., $(A.NH_3)_2Ca_{m-1}Ni_mO_{2m}$, m=1, 2, 3, ..., and $NH_3.A.NH_3MnO_3$, $(A.NH_3)_2MnO_3$, $NH_3.A.NH_3Ca_{m-1}MnO_{2m+2}$, m=1, 2, 3, ..., $(A.NH_3)_2Ca_{m-1}Mn_mO_{2m+2}$, m=1, 2, 3, . . . , $NH_3.A.NH_3RuO_3$, $(A.NH_3)_2RuO_3$, $NH_3.A.NH_3Ca_{m-1}Ru_mO_{2m+2}$, m=1, 2, 3, . . . , $(A.NH_3)_2Ca_{m-1}Ru_mO_{2m+2}$, m=1, 2, 3, . . . . These may be doped with carriers in the same ways as described above. The wide variety of these materials provide for different types of magnetic ordering (e.g. just by altering the structure from staggered to eclipsed) and other correlated states such as charge density waves and low-dimensional superconductivity. The discovery of surface superconductivity at 91K on the surface of lightly doped $Na_xWO_3$ single crystals [see Y. Levi et al., "*Europhys. Lett.* 51, 564 (2000]) raises the prospect of high temperature superconductivity in the present novel two-dimensional compounds.

Further monodentate molecules which may be used in the organic spacer layer include biphenylamine, $C_6H_5.C_6H_4.NH_2$, thiophenamine, $C_4SH_3.NH_2$, bithiophenamine, $C_4SH_3.C_4SH_2.NH_2$, and trithiophenamine, $C_4SH_3.(C_4SH_2)_2NH_2$. Further bithiophenamine, molecules which may be used in the organic spacer layer include biphenyldiamine, $NH_2.(C_6H_4)_2.NH_{2bi}$, diaminothiophene, $NH_2.C_4SH_2.NH_2$, diaminothiophene, $NH_2.(C_4SH_2)_2.NH_2$, and diaminothiophene, $NH_2.(C_4SH_2)_3.NH_2$. These and other conjugated molecules offer the possibility of conducting organic spacer layers and also the possibility of polymerisation of the organic spacer layer. Control of the interlayer coupling between inorganic oxide layers using conducting organic molecules provides a key means to control the phase behaviour and electronic properties of the novel oxides.

The compounds of the invention may be incorporated into devices by the production of films using methods known in the art such as spin coating, dip coating, spraying, painting, printing and such like.

Their great utility is that they self assemble by precipitation out of solution. They may then be dissolved in organic solvents and spin-coated onto suitable substrates and for example onto single-crystal perovskite substrates, such as $SrTiO_3$, with matching lattice parameters. The substrate lattice parameter may be selected to stabilise the films. Through careful heat treatment c-axis oriented films may be fabricated. Devices such as sensors, electrochromic films and thin-film field-effect transistors may be fabricated using these methods. Field-effect transistors may be made using the organic/inorganic-oxide as the semiconducting channel and device characteristics may be optimised by control of doping and of the spacing of the oxide layers. Sensor applications may be implemented based on the change in doping state induced by adsorbed gases.

A further means of assembling the present organic/inorganic oxide layered materials is to grow them onto self-assembled monolayers which are terminated by amine groups. It is well known that thiol-, isocyanide- or thioacetyl-terminated organic molecules self assemble onto gold substrates. If these molecules are terminated at the opposing end by an amine group then these molecules may be assembled as a monolayer onto gold then the organic/inorganic oxide material may be assembled onto the monolayer. Such amino-thiolated organic molecules for fabricating self-assembled monolayers include the 1-n aminoalkanethiols, $HS.(CH_2)_n.NH_2$ n=1, 2, 3, . . . , aminophenylthio $HS.C_6H_4.NH_2$, aminobiphenylthiol $HS.(C_6H_4)_2.NH_2$, amino-bithiophene-thiol $HS.(C_4SH_2)_2.NH_2$, and other related compounds. Variations of these, including the separation of amine or thiol groups from the phenyl groups using alkane chains, and the replacement of thiol groups by cyanide groups or thioacetyl groups in all of the above will be obvious extensions within the scope of the present invention.

BRIEF DESCRIPTION OF THE FIGURES

The invention is described with reference to the Figures in which:

With specific reference to the figures:

FIG. 1 shows a schematic diagram of a plan view of the structure of $WO_3$ (or $MoO_3$) in which the corner-shared $WO_6$ octahedra are represented by the shaded corner-shared diamonds, 1. Doping is achieved by substituting cations into the vacant 12-coordinated perovskite A-sites.

FIG. 2 shows a schematic diagram of a cross sectional side view of the structure of the hybrid organic/inorganic multilayered compound $NH_3ANH_3.WO_4$ where $NH_3ANH_3^{2+}$ may be a diammoniumalkane chain. The single atomic layer of $WO_6$ octahedra, 1 are again represented by the shaded diamonds and the $NH_3^+$ groups, 2 are represented by the circles at either end of the alkane chains, with the organic group A is represented by the ellipses.

FIG. 3 shows a schematic diagram of a cross sectional side view of the structure of the two-layer hybrid organic/inorganic multilayered compound $NH_3ANH_3.W_2O_7$ where $NH_3ANH_3^{2+}$ may be a diammoniumalkane chain. The single atomic layer of $WO_6$ octahedra, 1 are again represented by the shaded diamonds and the $NH_3^+$ groups, 2 are represented by the circles at either end of the alkane chains, with the organic group A is represented by the ellipses. In general, any number of oxide layers may be interspersed between the organic spacer layers providing the general formula $NH_3ANH_3.W_mO_{3m+1}$.

FIG. 4 shows a schematic diagram of a cross sectional side view of the structure of the staggered hybrid organic/inorganic-oxide multilayered compound $(ANH_3)_2WO_4$ where A is an organic molecule represented by the ellipse. The $WO_6$ octahedra, 1 are again represented by the shaded corner-shared diamonds and the $NH_3^+$ groups, 2 by the circles.

FIG. 5 shows a schematic diagram of the structure of the $2^{nd}$ member of the general staggered structural series $(A.NH_3)_2W_nO_{3n+1}$. The double layer of $W_2O_7$ is shown by the double layer of shaded corner-shared diamonds and the interdigitated ellipses A represent alkyl or aromatic organic groups terminated by ammonium ions, 2 (circles).

FIG. 6 shows the x-ray diffraction pattern for diammonium-hexane-tungstate as described in example 2.

FIG. 7 shows a plot of c-axis spacing as a function of alkane number, n, for diammonium-alkane-tungstate prepared at pH□10 for n=2, 6 and 12 as described in examples 2, 3 and 4.

FIG. 8 shows a plot of c-axis spacing as a function of alkane number, n, for diammonium-alkane-tungstate prepared at pH◻10 and pH◻6 for n=2, 6 and 12 as described in example 5.

FIG. 9 shows a scanning electron micrograph of phenylenediammonium-tungstate powder prepared at pH◻10 as described in example 10.

FIG. 10 shows a scanning electron micrograph of phenylenediammonium-tungstate powder prepared at pH◻1.5 as described in example 10.

EXAMPLES

Example 1

A quantity 3.429 g of $H_2WO_4$ was weighed out and dissolved in 60 ml of ammonia solution with gentle heating to 70° C. After cooling 3 ml of Benzylamine was added and the mixture stirred and heated under flowing nitrogen. The excess ammonia was evaporated off slowly, leaving the wet precipitate, which was then filtered and dried.

X-ray Diffraction was performed on the resultant white powder. The powder diffraction pattern revealed a major peaks corresponding to d-spacings of 16.48 Å and 15.59 Å. One of these, possibly the smaller, is consistent with the expected lattice parameter for dibenzylammonium tungstate, $(C_6H_5CH_2NH_3)_2WO_4$. The other compound is as yet unidentified.

A film was made by redissolving some of the powder in anhydrous ethanol, spinning onto a $SrTiO_3$ single-crystal substrate at 2000 rpm and drying for 15 minutes under flowing nitrogen gas at 80° C.

Example 2

Figure 1:
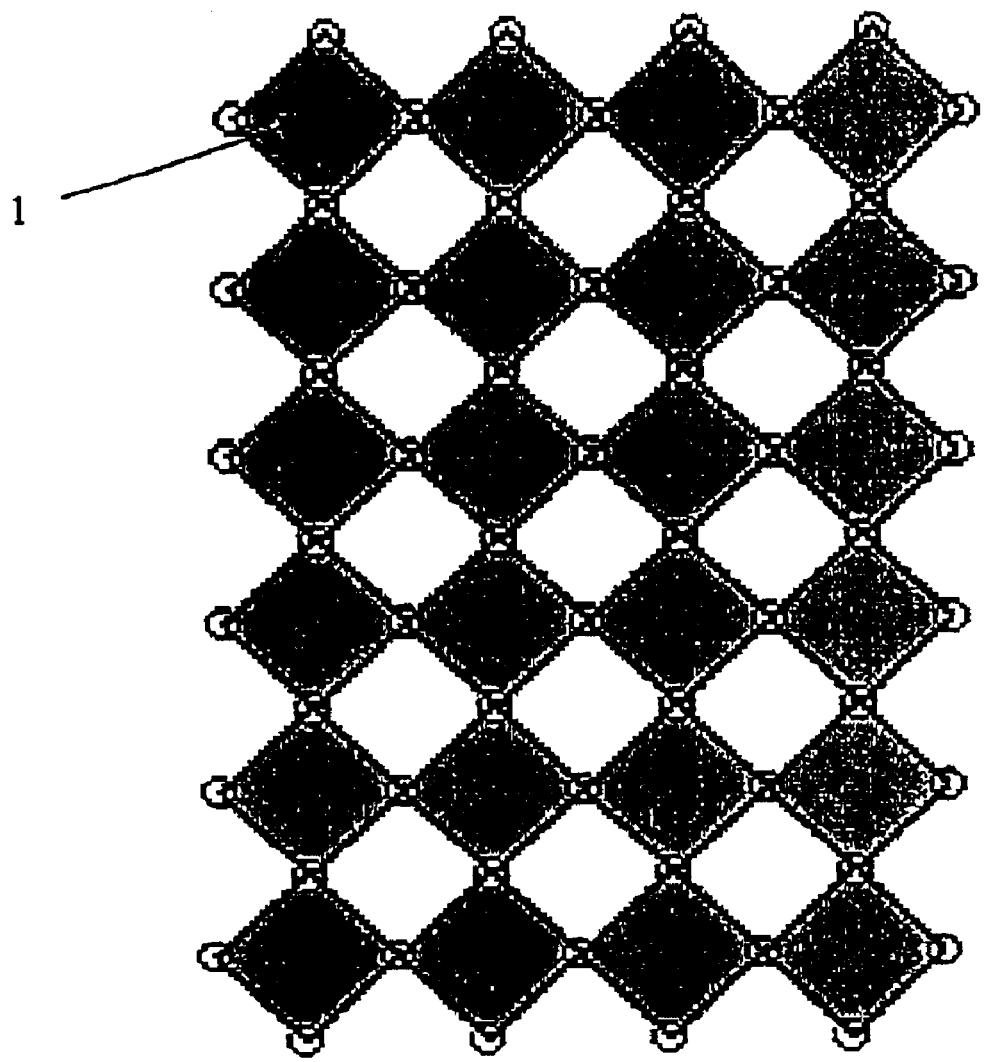
FIG. 1: illustrates a schematic plan view of the structure of $WO_3$ or $MoO_3$.
Figure 2:
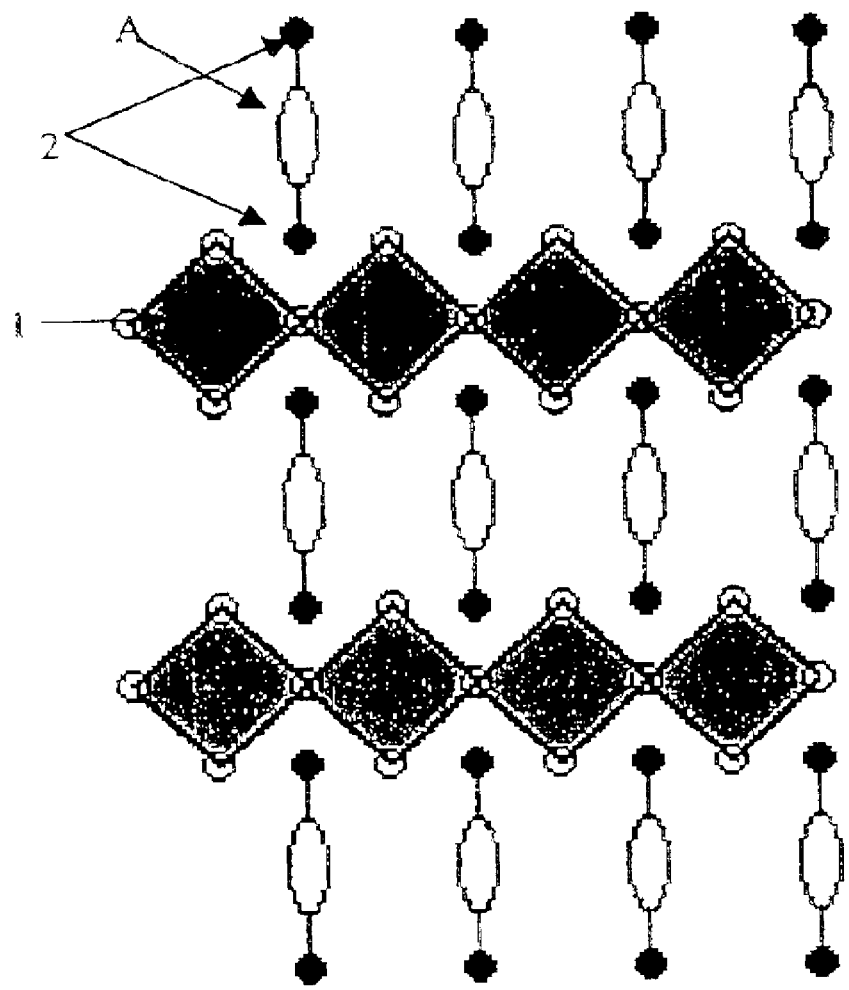
FIG. 2: illustrates a schematic side cross section view of one material in accordance with the invention.
Figure 3:
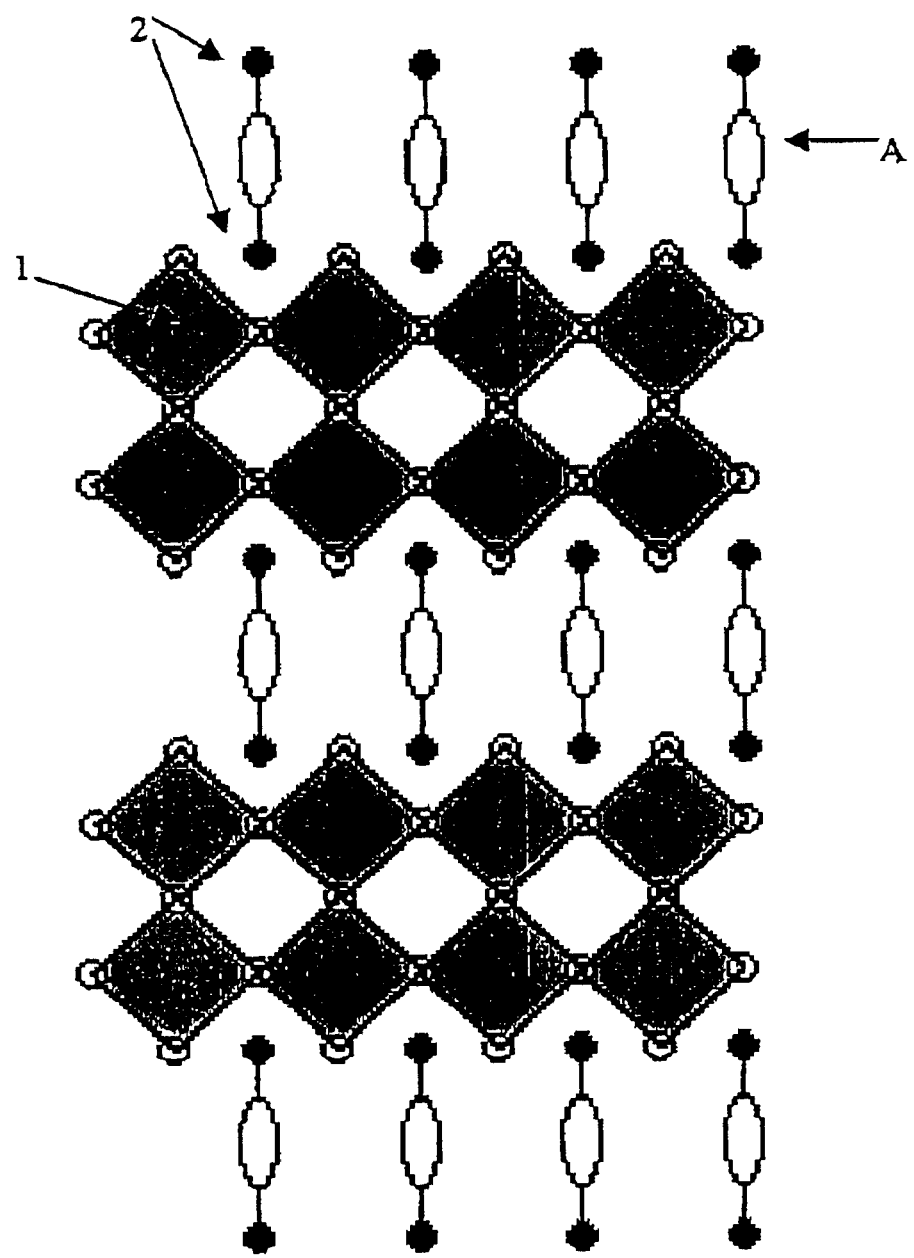
FIG. 3: illustrates a schematic side cross section view of a second material in accordance with the invention.
Figure 4:
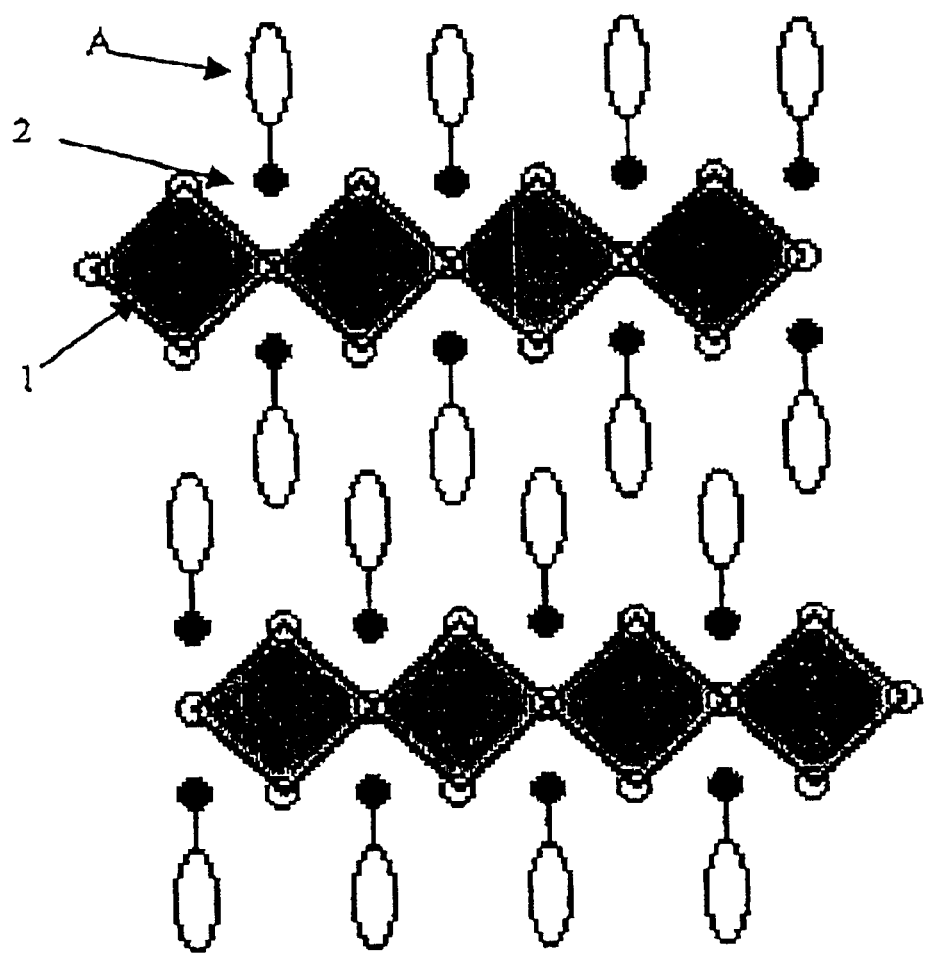
FIG. 4: illustrates a schematic side cross section view of a further material in accordance with the invention.
Figure 5:
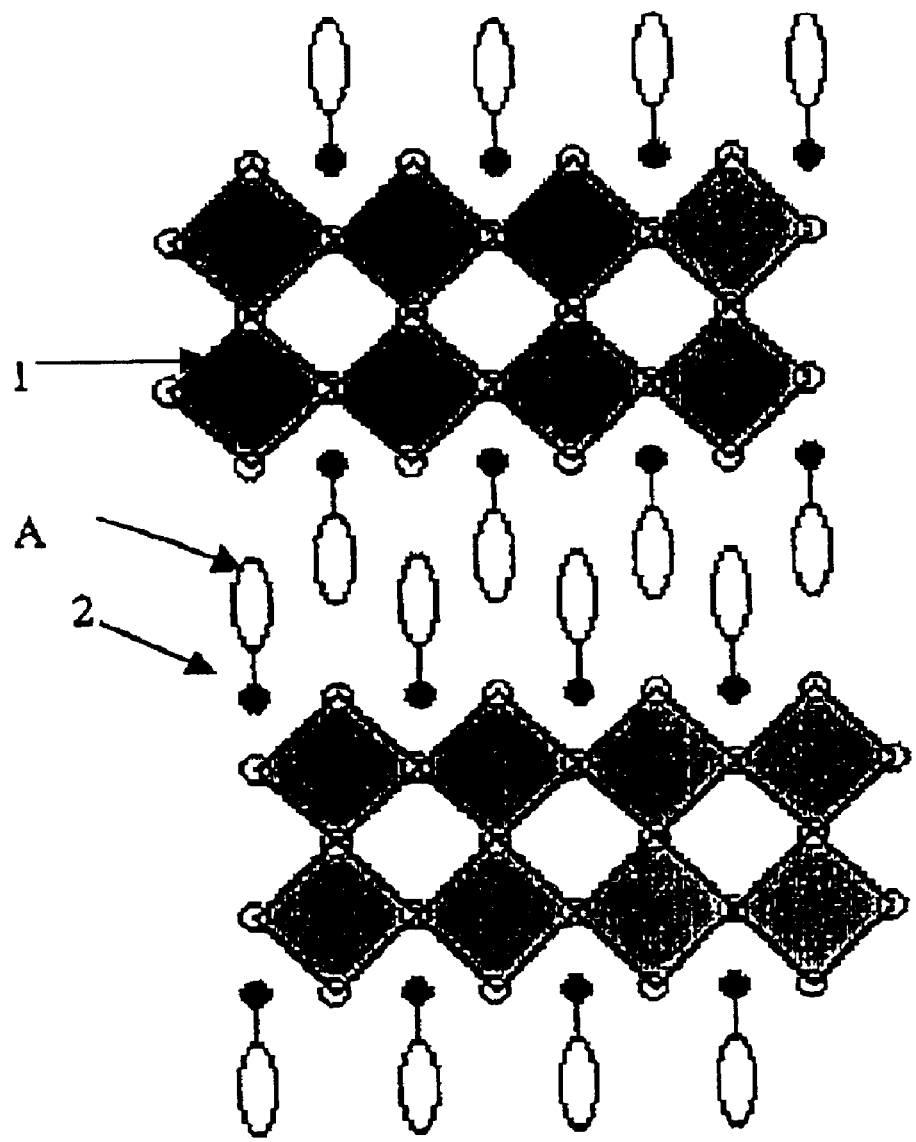
FIG. 5: illustrates a schematic side cross section view of a further material in accordance with the invention.
Figure 6:
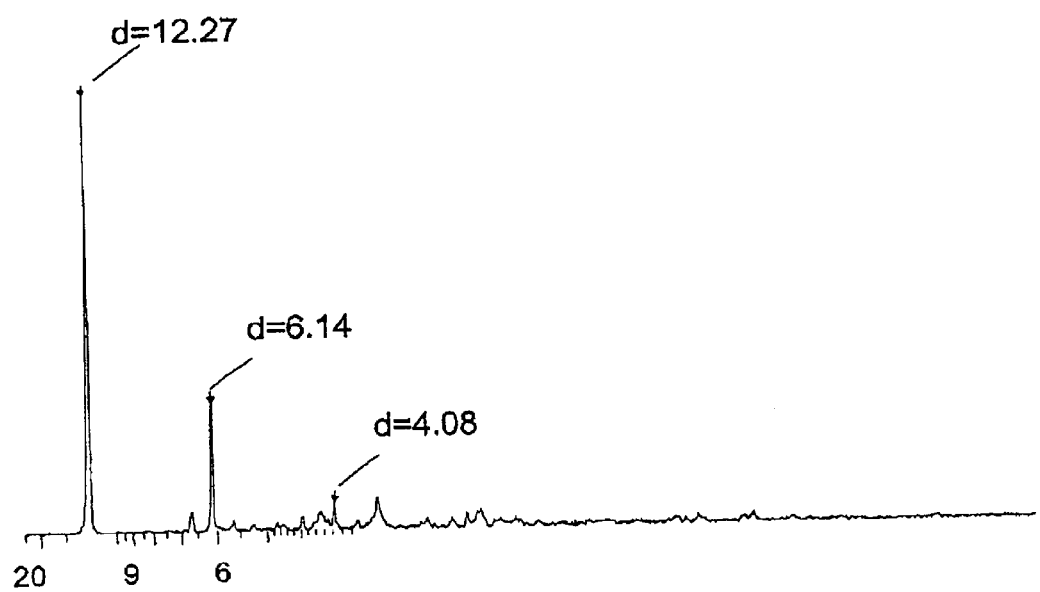
FIG. 6: illustrates an XRD pattern of one material of the invention.

Hybrid organic/inorganic oxide materials were synthesized by reacting diaminoalkanes with tungstic acid in stoichiometric proportions. Tungstic acid $H_2WO_4$ was dissolved in ammonia solution and 1–6 diaminohexane was separately dissolved in ammonia solution. The two solutions were mixed in stoichiometric proportions and the resulting solution, with pH of about 10, was heated at 90° C. to evaporate the ammonia The pH remained about 9.5 once the ammonia had evaporated. The solution was then heated at 80° C. to evaporate the remaining water and a powder precipitated. The powder was subjected to x-ray powder diffraction (XRD) and the XRD pattern is shown in FIG. 6. The marked diffraction lines correspond to the 001, 002 and 003 reflections of a layered compound with c-axis lattice parameter c=12.27 Å. The compound is identified as the novel compound diammoniumhexane-tungstate with formula $(NH_3)_2(CH_2)_6WO_4$.

Example 3

The process of example 2 was repeated but using 1–2 diaminoethane dissolved in ammonia solution. The XRD pattern of the resultant powder revealed a c-axis spacing of 7.39 Å. The compound is identified as the novel compound diammoniumethane-tungstate with formula $(NH_3)_2(CH_2)_2WO_4$.

Example 4

Figure 7:
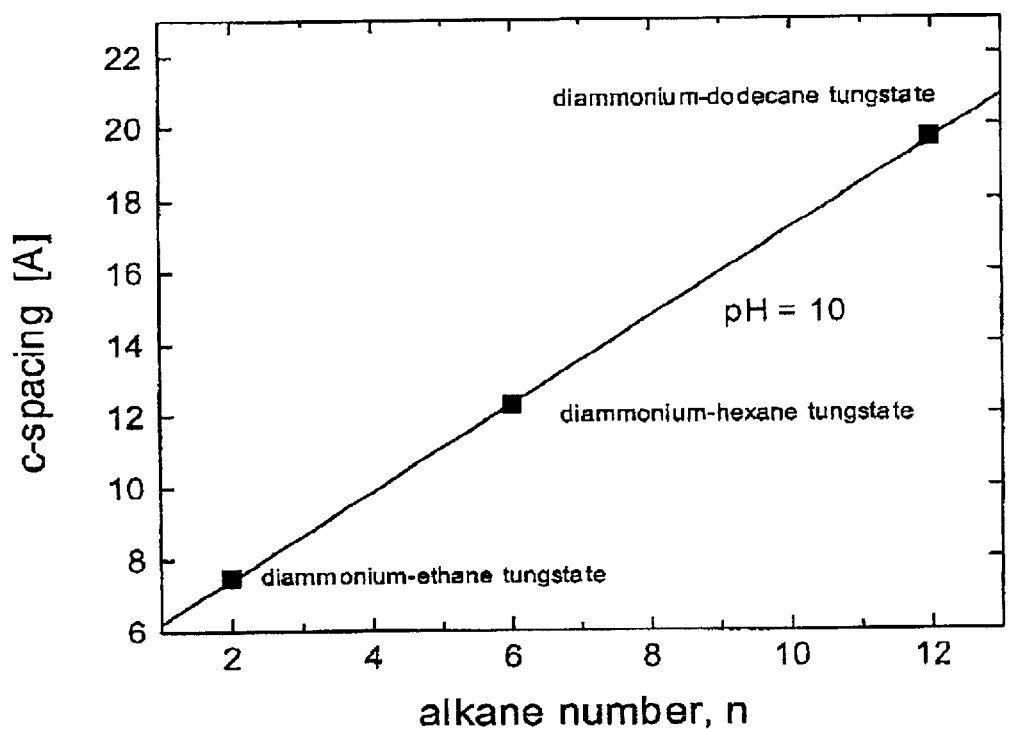
FIG. 7: is a plot of c-axis spacing vs alkane number.

The process of example 2 was repeated but using 1–12 diaminododecane dissolved in ethanol. The XRD pattern of the resultant powder revealed a c-axis spacing of 19.59 Å. The compound is identified as the novel compound diammoniumdodecane-tungstate with formula $(NH_3)_2(CH_2)_{12}WO_4$. The c-axis spacings for the products of examples 2, 3 and 4 are plotted as a function of alkane number in FIG. 7. The result is a straight line of equation c=1.22n+4.99 Å. This is consistent with the alkane chains in each compound being aligned perpendicular to the tungstic oxide layers and the nitrogen atoms in the ammonium groups lying in the vacant perovskite Z sites in the plane of the apical oxygen atoms in the $ZMO_3$ structure, Firstly the additional c-axis spacing (1.22 Å) for each additional carbon atom in the chain length is consistent with the C—C bond-length of 1.54 Å and the C—C—C bond angle of 109.28°, giving a C—C spacing projected along the length of the alkane chain of 1.25 Å. Now consider the offset, $d_0$, between the nitrogen atoms in the ammonium groups and the vacant perovskite Z sites in the $ZMO_3$ structure. The intercept value of 4.99 Å comprises the W—W bondlength (3.75 Å) and a projected C—N bondlength (1.22 Å) plus the offset $d_0$, namely 4.99=3.75+1.22+$d_0$. Clearly $d_0$ is essentially zero. These compounds therefore form model eclipsed structures comprising a single atomic layer of $WO_4$ consisting of a corner-shared $WO_2$ layer capped above and below by apical oxygens completing the octahedral coordination of W. The diammonium alkane chains extend perpendicular to these $WO_4$ layers with the N atom sited approximately in the plane of the apical oxygen atoms and in the face-centred location as if the $NH_3$ group were the Z atom in the perovskite $ZMO_3$ structure. Scanning electron microscopy shows these materials to exhibit a very flat micaceous crystallites consistent with their layered structure.

Example 5

Figure 8:
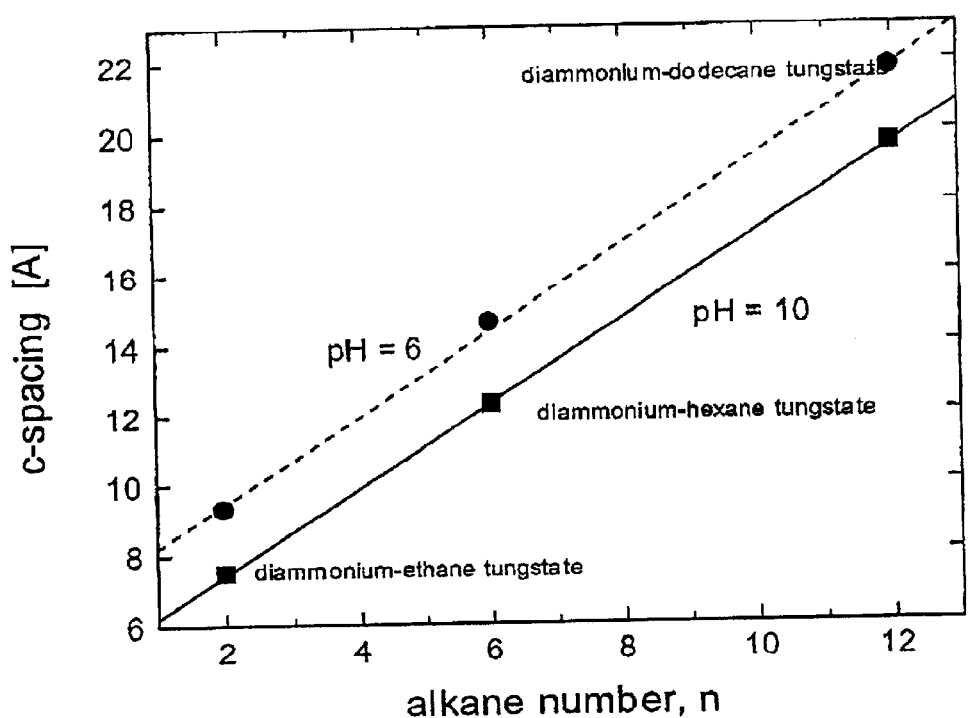
FIG. 8: is a plot of c-axis spacing vs alkane number.

Examples 2, 3 and 4 were repeated with the exception that the pH off he mixed solution was lowered by adding either hydrochloric acid or nitric acid. As described in the examples, at pH about 10 the canonical layered diaminoalkane tungstates were produced. At pH about 8, and for both acids, a purely inorganic oxide precipitated out, that is having no organic component. This was identified using XRD to be ammonium tungstate $(NH_4)_{10}W_{12}O_{41}$. At pH 6 or lower HCL resulted again in the formation of $(NH_4)_{10}W_{12}O_{41}$ but $HNO_3$ resulted in powders with a large c-axis spacing and these powders were not single phase. FIG. 8 shows the c-spacings obtained in this way at pH=6 for n=2, 6 and 12 plotted as a function of the alkane number n. They yield a straight line fit of c=1.22n+6.96. These novel materials therefore have a c-spacing which is 2 Å larger than that of the canonical layered organic/inorganic materials. Synchrotron x-ray diffraction reveal these to consist of an ordered array of oval shells of tungsten oxide separated by diammoniumalkane chains. These are not canonical layered organic/inorganic materials which evidently require pH in excess of 8 to form.

Example 6

Examples 2, 3 and 4 were repeated using molybdic acid, in the form of ammonium dimolybdate, instead of tungstic acid. This resulted at high pH in the same canonical layered organic inorganic materials of chemical formula $(NH_3)_2(CH_2)_nWO_4$ for n=2, 6 and 12. Scanning electron microscopy showed these also to have flat crystallites.

Example 7

Benzylamine and tungstic acid were reacted in stoichiometric proportions as described in example 2. After evaporation of ammonia and water a white powder was obtained. This showed a single-phase layered structure with lattice c-parameter of 16.5 Å. This is a canonical layered organic/inorganic oxide of formula $(C_6H_5CH_2NH_3)_2WO_4$.

Example 8

Analine and tungstic acid were reacted in stoichiometric proportions as described in example 2 at pH≈10. After evaporation of ammonia and water a white powder was obtained. This revealed ammonium tungstate, $(NH_4)_{10}W_{12}O_{41}$, as the dominant phase and the absence of any canonical layered organic/inorganic/oxide. The example was repeated at pH=6 with the same result. The example was repeated using molybdic acid with the same result.

Example 9

Phenethylamine, $C_6H_5(CH_2)_2NH_2$ and tungstic acid were reacted in stoichiometric proportions as described in example 2 at pH≈10. After evaporation of ammonia and water a white powder was obtained. This showed a single-phase layered structure. This is a canonical layered organic/inorganic oxide phenethylammonium tungstate of formula $(C_6H_5(CH_2)_2NH_3)_2WO_4$.

Example 10

Figure 9:
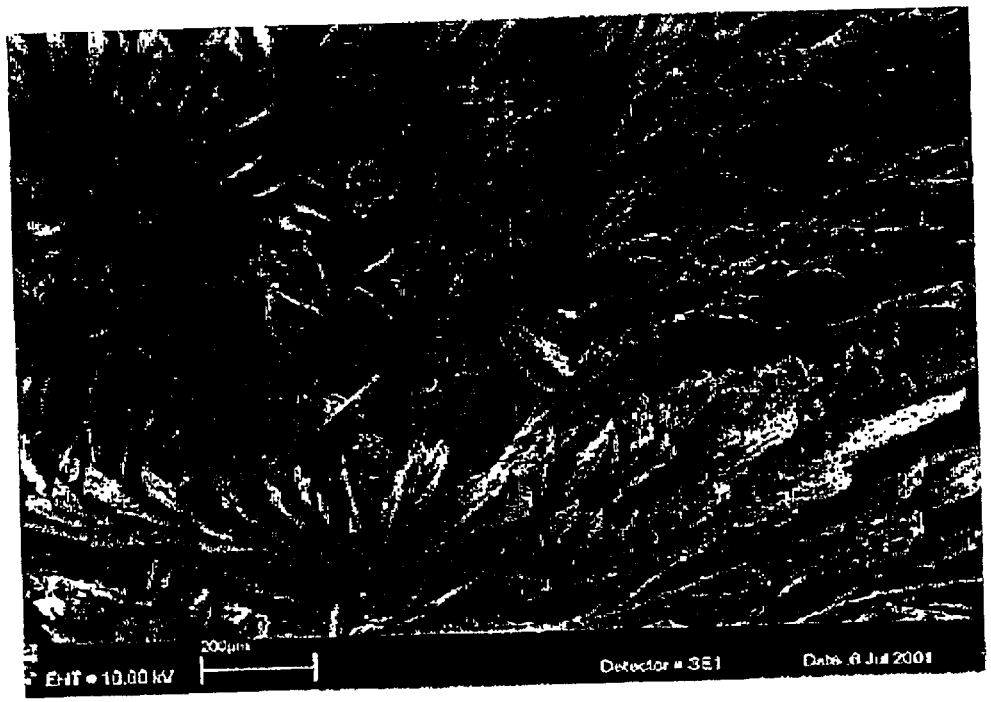
FIG. 9: is a scanning electron micrograph of a material of the invention.
Figure 10:
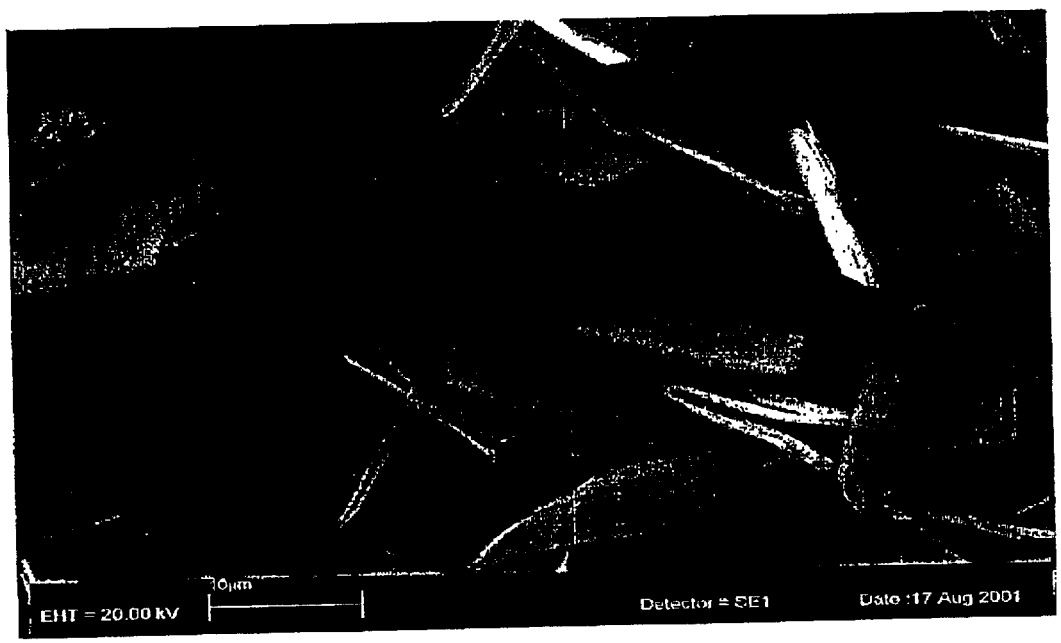
FIG. 10: is a scanning electron micrograph of a material of the invention.

Phenylenediamine, $NH_2C_6H_4NH_2$ and tungstic acid were reacted in stoichiometric proportions as described in example 2 at pH≈10. After evaporation of ammonia and water a black powder was obtained. XRD of this powder revealed a layered structure with lattice d-spacings of 14.2 Å and 12.8 Å. The scanning electron micrograph shown in FIG. 9 indicates crystallites in the form of flat sheets consistent with their layered structure. The example was repeated at pH≈1.5. The resultant crystallites were very flat and platey as shown in FIG. 10 with d-spacing 12.6 Å.

Example 11

Example 10 was repeated using molybdic acid in the form of ammonium dimolybdate. The powder precipitated at pH≈10 was examined by visible and UV spectroscopy. This revealed an apparent plasma edge at 1.5 eV consistent with the formation of conductive phenylenediammonium links between the oxide layers. The example was repeated at pH≈1.5. Flat crystallites were obtained with d-spacing≈12.8 Å.

What is claimed is:

1. A layered organic-inorganic/oxide material comprising one or more layers of a metal oxide and one or more layers of organic molecules, wherein the metal-oxide layers alternate with one or more organic layers alternate to form a periodic planar structure.

2. The layered organic-inorganic/oxide material as claimed in claim 1 wherein the one or more layers of the metal oxide comprise one or more atomic planes of corner-shared $MO_6$ octahedra, where M is a metal.

3. The material as claimed in claim 2 wherein the metal M is W, V or Mo, or a combination of these.

4. The material as claimed in claimed 3 wherein a high valency metal selected from the group consisting of Ti, Nb, Ta, Ru and Re is used in partial combination with M.

5. The material as claimed in claim 3 having a general formula $X.M_mO_{3m+1}$ wherein M is the metal, and X is an organic cation and m=1, 2, or 3.

6. The material as claimed in claim 5 wherein the organic cation is bidentate.

7. The material as claimed in claim 6 wherein the configuration of organic layer relative to the inorganic layer is eclipsed.

8. The material as claimed in claim 6 wherein the organic cation is a diammonium cation, the material is of composition $NH_3.A.NH_3.M_mO_{3m+1}$, wherein "A" is an organic group.

9. The material as claimed in claim 8 wherein m=1, such that there are a plurality of inorganic oxide atomic planes each alternating with an organic layer.

10. The material as claimed in claim 9 wherein the organic cation is an aliphatic diammonium cation, and $A=(CH)_{n2}$ n=1,2, . . . .

11. The material as claimed in claim 10 wherein, on the organic cation, A includes terminal alkane units and the ammonium cation groups are positioned on the terminal alkane units of A.

12. The material as claimed in claim 11 having the chemical formula $NH_3(CH_2)_nNH_3MO_4$.

13. The material as claimed in claim 12 with n=2.

14. The material as claimed in claim 12 with n=6.

15. The material as claimed in claim 12 with n=12.

16. The material as claimed in claim 8 wherein m=2, the composition is $NH_3.A.NH_3.M_2O_7$ and wherein the inorganic oxide exists as double atomic plane layer of corner shared $MO_6$ octahedra, such that the material has the stacking structure —A—O—$MO_2$—O—$MO_2$—O—A.

17. The material as claimed in claim 5 wherein the organic cation is an aromatic diammonium cation.

18. The material as claimed in claim 17 wherein the organic cation is α-ω$NH_3C_6H_4NH_3$.

19. The material as claimed in claim 18 in which there are two or more aromatic rings at least two of which are adjacent and where the adjacent aromatic rings are crosslinked to form an organic polymer layer.

20. The material as claimed in claim 19 in which the organic polymer layer is conducting.

21. The material as claimed in claim 17 wherein the organic cation comprises an aromatic ring with two aliphatic side chains of equal or unequal length each side chain terminated by an ammonium ion, the organic cation having the general formula $NH_3(CH_2)_pC_6H_4(CH_2)_qNH_3$, where "p" and "q" are each independently selected from 0, 1, 2, or 3.

22. The material as claimed in claim 17 wherein the aromatic diammonium cation has a string of one or more aromatic moieties of phenylene.

23. The material as claimed in claim 3 having a general formula $X'_2.M_mO_{3m+1}$ wherein M is the metal, and X' is an organic cation and m=1, 2, 3.

24. The material as claimed in claim 23 wherein the organic cation is monodentate.

25. The material as claimed in claim 23 wherein the configuration of organic layer relative to the inorganic layer is staggered.

26. The material as claimed in claim 25 wherein both organic cations are monoammonium cations and the material is of composition $(NH_3.A')_2.M._mO_{3m+1}$ wherein A' is an organic group.

27. The material as claimed in claim 26 wherein m=1, such that each inorganic oxide atomic layer alternates with an organic layer.

28. The material as claimed in claim 26 wherein m=2, the composition is $(NH_3.A')_2.M_2O_7$ and wherein the organic oxide exists as a double atomic plane layer having approximately the $ZWO_3$ perovskite structure with the Z sites vacant such that the material has the stacking structure $NH_3.A'$—$MO_2$—O—$MO_2$—$A'.NH_3$.

29. The material as claimed in claim 27 or 28 wherein one or both organic cation is an aliphatic ammonium cation, and $A'=(CH)_n$, n=1, 2, . . . .

30. The material as claimed in claim 27 wherein one or both organic cation is an aromatic ammonium cation.

31. The material as claimed in claim 30, wherein the aromatic ammonium cation has an aromatic ring and the aromatic ring has a side chain which is aliphatic and terminated by an ammonium ion, having the formula $(C_6H_5.(CH_2)_m NH_3)_2 MO_4$ where m=0, 1, 2, 3, ....

32. The material as claimed in claim 30 in which the aromatic ammonium cation has two or more aromatic rings, at least tow of which are adjacent, and wherein the adjacent aromatic rings are crosslinked to form an organic polymer layer.

33. The material as claimed in claim 32 in which the organic polymer layer is conducting.

34. A material as claimed in claim 33 wherein dopants are introduced into the structure.

35. A material as claimed in claim 33 in which M is partially or fully substituted by a magnetic transition metal ion so as to display magnetically ordered states.

36. An organic/inorganic oxide material of claim 33 in which the oxide layer comprising $MO_4$, $M_2O_7$ or $M_mO_{3m+1}$ is wholly replaced by any of the following oxide layers $CuO_2$, $NiO_2$, $CoO_2$, $CuO_2CaCuO_2$, $Ca_{m-1}Cu_mO_{2m}$, m=1, 2, 3, ..., $NiO_2CaNiO_2$, $Ca_{m-1}Ni_mO_{2m}$, m=1, 2, 3, ..., square pyramidal $MnO_3$, square pyramidal $RuO_3$, octahedral $RuO_4$, O—$Mn_2$—Y—$MnO_2$—O, O—$MnO_2$—Ca—$MnO_2$—O, O—$RuO_2$—Y$RuO_2$—O, or O—$RuO_2$—Ca—$RuO_2$—O.

37. The material as claimed in claim 30 wherein the aromatic diammonium cation has a string of one or more aromatic moieties of phenylene.

38. The material as claimed in claim 32 wherein dopants are introduced into the structure.

39. The material as claimed in claim 38 wherein the dopant is selected from one or more of an alkali cation, a methyl ammonium cation the cations replacing ammonium groups, field-effect injected electrons or field-effect injected electron holes.

40. A material as claimed in claim 39 in which M is partially or fully substituted by a magnetic transition metal ion so as to display magnetically ordered states.

41. The material as claimed in claim 38 wherein the dopant is present in the inorganic oxide layers and the doping state of the oxide is adjusted such that the oxide exhibits superconductivity above the temperature of 40 K.

42. A material as claimed in claim 41 in which M is partially or fully substituted by a magnetic transition metal ion so as to display magnetically ordered states.

43. The material as claimed in claim 38 where the doping state of the oxide is adjusted such that the oxide exhibits superconductivity above the temperature of 90 K.

44. A material as claimed in claim 43 in which M is partially or fully substituted by a magnetic transition metal ion so as to display magnetically ordered states.

45. A material as claimed in claim 38 in which M is partially or fully substituted by a magnetic transition metal ion so as to display magnetically ordered states.

46. An organic/inorganic oxide material of claim 38 in which the oxide layer comprising $MO_4$, $M_2O_7$ or $M_mO_{3m+1}$ is wholly replaced by any of the following oxide layers $CuO_2$, $NiO_2$, $CoO_2$, $CuO_2CaCuO_2$, $Ca_{m-1}Cu_mO_{2m}$, m=1, 2, 3, ..., $NiO_2CaNiO_2$, $Ca_{m-1}Ni_mO_{2m}$, m=1, 2, 3, ..., square pyramidal $MnO_3$, square pyramidal $RuO_3$, octahedral $RuO_4$, O—$Mn_2$—Y—$MnO_2$—O, O—$MnO_2$—Ca—$MnO_2$—O, O—$RuO_2$—Y$RuO_2$—O, or O—$RuO_2$—Ca—$RuO_2$—O.

47. The material of claim 2 in which M is partially or fully substituted by a magnetic transition metal ion so as to display magnetically ordered states.

48. The organic/inorganic oxide material of claim 2 in which the oxide layer comprising $MO_4$, $M_2O_7$ or $M_mO_{3m+1}$ is wholly replaced by any of the following oxide layers $CuO_2$, $NiO_2$, $CoO_2$, $CuO_2CaCuO_2$, $Ca_{m-1}Cu_mO_{2m}$, m=1, 2, 3, ..., $NiO_2CaNiO_2$, $Ca_{m-1}Ni_mO_{2m}$, m=1, 2, 3, ..., square pyramidal $MnO_3$, square pyramidal $RuO_3$, octahedral $RuO_4$, O—$Mn_2$—Y—$MnO_2$—O, O—$MnO_2$—Ca—$MnO_2$—O, O—$RuO_2$—Y$RuO_2$—O, or O—$RuO_2$—Ca—$RuO_2$—O.

49. The layered organic-inorganic oxide material as claimed in claim 1 wherein the one or more layers of metal oxide comprise one or more atomic planes of metal oxide having substantially the $ZMO_3$ perovskite structure (M=metal) with the Z sites vacant, and wherein the metals form divalent cations and are coordinated into a corner-shared square-planar structure, or the metals form tetravalent cations and are coordinated into a corner-shared square-pyramid structure.

50. The material as claimed in claim 49 wherein the metal, M, is Cu, Ni, Ru, Mn, or a combination of these.

51. The material as claimed in claim 50 wherein higher order structures are formed with two or more oxide layers each separated by an alkali earth ion which is situated in the perovskite Z-site.

52. The material as claimed in claim 51 wherein the alkali earth ion is calcium.

53. A material as claimed in claim 52 having the general formula of one of: $NH_3.A.NH_3CuO_2$, $(A.NH_3)_2CuO_2$, $NH_3.A.NH_3Ca_{m-1}Cu_mO_{2m}$, m=1, 2, 3, ..., $(A.NH_3)_2Ca_{m-1}Cu_mO_{2m}$, m=1, 2, 3, ..., $NH_3.A.NH_3NiO_2$, $(A.NH_3)_2NiO_2$, $NH_3.A.NH_3Ca_{m-1}Ni_mO_{2m}$, m=1, 2, 3, ..., $(A.NH_3)_2Ca_{m-1}Ni_mO_{2m}$, m=1, 2, 3, ..., and $NH_3.A.NH_3MnO_3$, $(A.NH_3)_2MnO_3$, $NH_3.A.NH_3Ca_{m-1}Mn_mO_{2m+2}$, m=1, 2, 3, ..., $(A.NH_3)_2Ca_{m-1}Mn_mO_{2m+2}$, m=1, 2, 3, ..., $NH_3.A.NH_3RuO_3$, $(A.NH_3)_2RuO_3$, $NH_3.A.NH_3Ca_{m-1}Ru_mO_{2m+2}$, m=1, 2, 3, ..., $(A.NH_3)_2Ca_{m-1}Ru_mO_{2m+2}$, m=1, 2, 3, ..., wherein "A" is an organic group.

54. A material as claimed in claim 53 in which M is partially or fully substituted by a magnetic transition metal ion so as to display magnetically ordered states.

55. The material as claimed in any one of claims 49 to 53 wherein dopants are introduced into the structure.

56. The material as claimed in claim 55 wherein the dopant is selected from one or more of an alkali cation, a methyl ammonium cation the cations replacing ammonium groups, field-effect injected electrons or field-effect injected electron holes.

57. The material as claimed in claim 56 wherein the dopant is present in the inorganic oxide layers and the doping state of the oxide is adjusted such that the oxide exhibits superconductivity above the temperature of 40 K.

58. A material as claimed in claim 57 in which M is partially or fully substituted by a magnetic transition metal ion so as to display magnetically ordered states.

59. The material as claimed in claim 56 wherein the doping state of the oxide is adjusted such that the oxide exhibits superconductivity above the temperature of 90 K.

60. A material as claimed in claim 59 in which M is partially or fully substituted by a magnetic transition metal ion so as to display magnetically ordered states.

61. A material as claimed in claim 56 in which M is partially or fully substituted by a magnetic transition metal ion so as to display magnetically ordered states.

62. A material as claimed in claim 55 in which M is partially or fully substituted by a magnetic transition metal ion so as to display magnetically ordered states.

63. A material as claimed in claim 52 in which M is partially or fully substituted by a magnetic transition metal ion so as to display magnetically ordered states.

64. A material as claimed in claim 51 in which M is partially or fully substituted by a magnetic transition metal ion so as to display magnetically ordered states.

65. A material as claimed in claim 50 in which M is partially or fully substituted by a magnetic transition metal ion so as to display magnetically ordered states.

66. The material as claimed in claim 49 in which M is partially or fully substituted by a magnetic transition metal ion so as to display magnetically ordered states.

67. A method of preparing the layered inorganic-organic material as claimed in claim 1 which comprises the step of contacting a source of metal and/or oxide with a source of the organic molecules such that a layer structure substantially self assembles.

68. The method as claimed in claim 67 wherein the material is of the general structure $NH_3.A.NH_3.M_mO_{3m+1}$, wherein A is an organic group and the material is prepared either: by reaction of a diaminoalkane with tungstic acid (when the metal is W) or molybdic acid (when the metal is Mo), by dissolution of tungstic acid (when the metal is W) or molybdic acid (when the metal is Mo) in an ammonia solution, or by reaction of W or Mo metal with hydrogen peroxide to form a tungstate or molybdate complex as a precursor for reaction with the ammonia solution.

69. A layered inorganic-organic material of the general structure $NH_3.A.NH_3.M_mO_{3m+1}$ prepared substantially according to the method of claim 68.

* * * * *